United States Patent

Van Mierlo et al.

(10) Patent No.: US 7,522,263 B2
(45) Date of Patent: Apr. 21, 2009

(54) LITHOGRAPHIC APPARATUS AND METHOD

(75) Inventors: Hubert Adriaan Van Mierlo, Maassluis (NL); Gert-Jan Heerens, Schoonhoven (NL); Hans Meiling, Waalre (NL); Antonius Gerardus Theodorus Maria Bastein, Leiden (NL); Jacques Cor Johan Van der Donck, Alphen aan den Rijn (NL); Hedser Van Brug, The Hague (NL)

(73) Assignee: ASML Netherlands B.V., Veldhoven (NL)

( * ) Notice: Subject to any disclaimer, the term of this patent is extended or adjusted under 35 U.S.C. 154(b) by 17 days.

(21) Appl. No.: 11/317,243

(22) Filed: Dec. 27, 2005

(65) Prior Publication Data

US 2007/0146657 A1 Jun. 28, 2007

(51) Int. Cl.
*G03B 53/42* (2006.01)
*G03B 27/52* (2006.01)
*G03B 27/54* (2006.01)
*G03F 9/00* (2006.01)

(52) U.S. Cl. .............. 355/53; 355/30; 355/67; 430/5

(58) Field of Classification Search .......... 355/53, 355/30, 72, 75, 67; 382/144; 430/5; 438/689; 356/237.5, 237.2
See application file for complete search history.

(56) References Cited

U.S. PATENT DOCUMENTS

| | | | |
|---|---|---|---|
| 4,837,447 A | 6/1989 | Pierce et al. | |
| 5,416,594 A * | 5/1995 | Gross et al. | 356/237.5 |
| 5,559,584 A | 9/1996 | Miyaji et al. | |
| 5,853,962 A | 12/1998 | Bowers | 430/331 |
| 5,917,590 A | 6/1999 | Greve | |
| 5,936,734 A | 8/1999 | Johs et al. | 356/364 |
| 6,038,015 A | 3/2000 | Kawata | |
| 6,055,742 A | 5/2000 | Kim | |
| 6,288,769 B1 | 9/2001 | Akagawa et al. | |
| 6,305,097 B1 | 10/2001 | Salamati-Saradh et al. | |
| 6,327,021 B1 | 12/2001 | Higashiguchi | |
| 6,392,738 B1 | 5/2002 | van de Pasch et al. | |
| 6,394,109 B1 | 5/2002 | Somekh | |

(Continued)

FOREIGN PATENT DOCUMENTS

JP 55-15620 2/1980

(Continued)

OTHER PUBLICATIONS

Official Action issued for Japanese Patent Application No. JP 2003-321110 dated Jan. 20, 2006.

(Continued)

*Primary Examiner*—Peter B Kim
(74) *Attorney, Agent, or Firm*—Sterne, Kessler, Goldstein & Fox P.L.L.C.

(57) ABSTRACT

A lithographic apparatus is disclosed. The apparatus includes an illumination system configured to condition an extreme ultraviolet radiation beam, a patterning device configured to impart the extreme ultraviolet radiation beam with a pattern in its cross-section to form a patterned extreme ultraviolet radiation beam, a substrate table constructed to hold a substrate, a projection system provided with reflective optics configured to project the patterned extreme ultraviolet radiation beam onto a target portion of the substrate, a vacuum chamber constructed to create a vacuum environment, and a detection unit arranged within the vacuum chamber to detect contamination on the patterning device.

20 Claims, 4 Drawing Sheets

U.S. PATENT DOCUMENTS

| | | |
|---|---|---|
| 6,395,102 B1 | 5/2002 | Salamati-Saradh et al. |
| 6,589,354 B2 | 7/2003 | Reid |
| 6,621,568 B1 * | 9/2003 | Yonezawa ............... 356/237.2 |
| 6,671,051 B1 | 12/2003 | Nikoonahad et al. |
| 6,694,284 B1 | 2/2004 | Nikoonahad et al. ........ 702/155 |
| 2002/0057425 A1 | 5/2002 | Nakano |
| 2002/0094685 A1 * | 7/2002 | Nakata et al. ............... 438/689 |
| 2003/0045098 A1 | 3/2003 | Verhaverbeke et al. |
| 2003/0058424 A1 | 3/2003 | Ramamoorthy et al. |
| 2003/0218728 A1 * | 11/2003 | del Puerto et al. ............. 355/51 |
| 2004/0125375 A1 | 7/2004 | Some ........................ 356/369 |
| 2004/0140298 A1 | 7/2004 | Widmann et al. |
| 2004/0150820 A1 | 8/2004 | Nikoonahad et al. |
| 2004/0180270 A1 * | 9/2004 | Heerens ........................ 430/5 |
| 2004/0185682 A1 | 9/2004 | Foulke et al. |
| 2004/0233442 A1 | 11/2004 | Mieher et al. |
| 2005/0016679 A1 | 1/2005 | Ruzic et al. ............. 156/345.5 |
| 2005/0030505 A1 | 2/2005 | Miwa |
| 2005/0058836 A1 | 3/2005 | Goldstein |
| 2006/0066854 A1 | 3/2006 | Meeks et al. |
| 2006/0082743 A1 | 4/2006 | Yonekawa et al. |
| 2006/0176460 A1 * | 8/2006 | Phillips et al. ................ 355/67 |
| 2007/0146658 A1 | 6/2007 | Van Mierlo et al. |
| 2007/0146695 A1 | 6/2007 | Brouwer et al. |

FOREIGN PATENT DOCUMENTS

| | | |
|---|---|---|
| JP | 58-21742 A | 2/1983 |
| JP | 61-10237 A | 1/1986 |
| JP | 61-159730 | 7/1986 |
| JP | 61-207953 | 9/1986 |
| JP | 62-62251 | 3/1987 |
| JP | 63-41855 | 2/1988 |
| JP | 3-155550 A | 7/1991 |
| JP | 6-283488 | 10/1994 |
| JP | 7-169663 | 7/1995 |
| JP | 8-78182 A | 3/1996 |
| JP | 8-124822 A | 9/1996 |
| JP | 8-321480 | 12/1996 |
| JP | 11-101742 A | 4/1999 |
| JP | 2000-58494 | 2/2000 |
| JP | 2001-358046 | 12/2001 |
| JP | 2003-022993 | 1/2003 |
| JP | 2004-141704 | 5/2004 |
| JP | 2004-152843 | 5/2004 |
| KR | 2001-0066292 A | 7/2001 |
| KR | 2001-0083591 A | 9/2001 |
| RU | 2 149 425 C1 | 5/2000 |
| WO | WO 2004/076963 A2 | 9/2004 |
| WO | WO 2004/095136 A2 | 11/2004 |
| WO | WO 2005/108914 A2 | 11/2005 |

OTHER PUBLICATIONS

International Search Report issued for PCT Patent Application No. PCT/NL2006/000605 dated Apr. 17, 2007.

Meiling et al., "The EUV Project at ASML: an update," Emerging Lithographic Technologies VII, Proceedings of SPIE, vol. 5037 (2003), pp. 24-35.

Postava et al., "Null Ellipsometer with Phase Modulation", Optics Express, vol. 12, No. 24, Nov. 29, 2004, pp. 6040-6045.

English Abstract of JP 58-21742 published Feb. 8, 1983, 2 pgs.

English Abstract of JP 61-10237 published Jan. 17, 1986, 1 pg.

English Abstract of JP 3-155550 published Jul. 3, 1991, 2 pgs.

English Abstract of JP 8-78182 published Mar. 22, 1996, 2 pgs.

English Abstract of JP 8-124822 published May 17, 1996, 2 pgs.

First Non-Final Office Action mailed Jun. 29, 2007 for U.S. Appl. No. 11/318,055, filed Dec. 27, 2005, 8 pgs.

Final Rejection mailed Dec. 28, 2007 for U.S. Appl. No. 11/318,055, filed Dec. 27, 2005, 11 pgs.

Second Non-Final Office Action mailed Jun. 11, 2008 for U.S. Appl. No. 11/318,055, filed Dec. 27, 2005, 9 pgs.

Third Non-Final Office Action mailed Dec. 17, 2008 for U.S. Appl. No. 11/318,055, filed Dec. 27, 2005, 9 pgs.

* cited by examiner

LITHOGRAPHIC APPARATUS AND METHOD

FIELD

The present invention relates to a lithographic apparatus and method.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g. comprising part of, one, or several dies) on a substrate (e.g. a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti-parallel to this direction. It is also possible to transfer the pattern from the patterning device to the substrate by imprinting the pattern onto the substrate.

Contamination of the patterning device is a problem in lithography. For example, dust or other contamination on the surface of the patterning device can result in a defect in the pattern which is applied to the substrate. The problem of contamination is particularly relevant to extreme ultra-violet (EUV) lithography, where due to the wavelength of the radiation used, certain protective elements (e.g. a protective pellicle on the patterning device) cannot be used to prevent contamination of the patterning device.

SUMMARY

It is desirable to provide a new apparatus and method for detecting contamination of the patterning device and/or removing contaminants from the patterning device.

According to a first aspect of the present invention, there is provided a lithographic apparatus. The apparatus includes an illumination system configured to condition an extreme ultraviolet radiation beam, a patterning device configured to impart the extreme ultraviolet radiation beam with a pattern in its cross-section to form a patterned extreme ultraviolet radiation beam, a substrate table constructed to hold a substrate, a projection system provided with reflective optics configured to project the patterned extreme ultraviolet radiation beam onto a target portion of the substrate, a vacuum chamber constructed to create a vacuum environment; and a detection unit arranged within the vacuum chamber to detect contamination on the patterning device.

According to a second aspect of the present invention, there is provided a method of detecting contamination on a patterning device of a lithographic apparatus provided with a vacuum chamber. The method includes moving the patterning device to a detection unit, and detecting contamination within the vacuum chamber with the detection unit.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION

Figure 1:
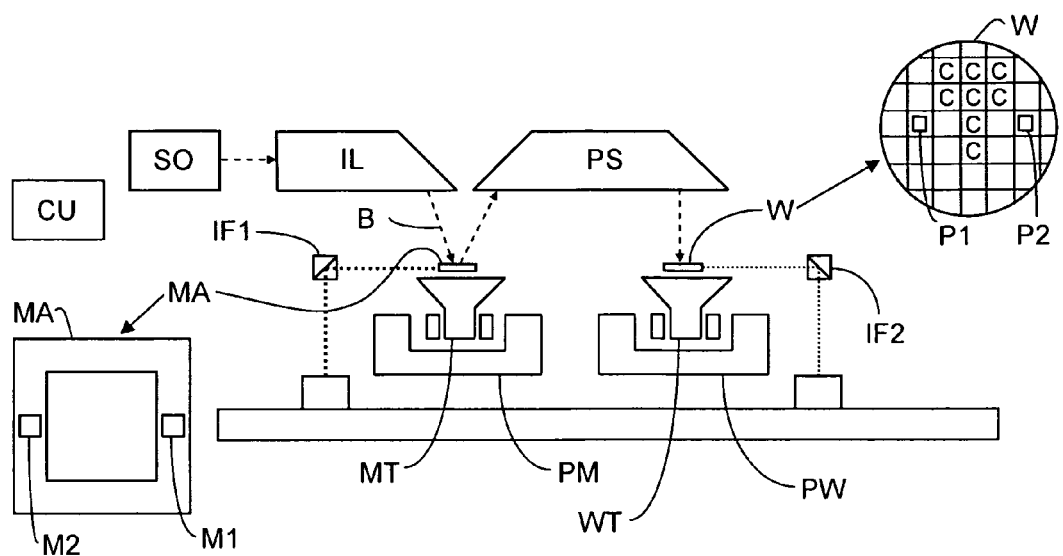
FIG. 1 depicts a lithographic apparatus provided with a cleaning unit according to an embodiment of the invention.

FIG. 1 schematically depicts a lithographic apparatus according to one embodiment of the invention. The apparatus comprises: an illumination system (illuminator) IL configured to condition a radiation beam B (e.g. UV radiation or EUV radiation); a support structure (e.g. a mask table) MT constructed to support a patterning device (e.g. a mask) MA and connected to a first positioner PM configured to accurately position the patterning device in accordance with certain parameters; a substrate table (e.g. a wafer table) WT constructed to hold a substrate (e.g. a resist-coated wafer) W and connected to a second positioner PW configured to accurately position the substrate in accordance with certain parameters; a projection system (e.g. a refractive projection lens system) PS configured to project a pattern imparted to the radiation beam B by patterning device MA onto a target portion C (e.g. comprising one or more dies) of the substrate W; and a cleaning unit CU arranged to clean the patterning device in-situ.

The illumination system may include various types of optical components, such as refractive, reflective, magnetic, electromagnetic, electrostatic or other types of optical components, or any combination thereof, for directing, shaping, or controlling radiation.

The support structure supports, i.e. bears the weight of, the patterning device. It holds the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" as used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam which is reflected by the mirror matrix.

The term "projection system" as used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a reflective type (e.g. employing a reflective mask). Alternatively, the apparatus may be of a transmissive type (e.g. employing a transmissive mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g. water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

The term "in-situ" as used herein should be interpreted as meaning substantially within the lithographic apparatus, enclosed by the lithographic apparatus or in communication with the lithographic apparatus such that, for example, a vacuum used to reduce contamination of the lithographic apparatus need not be destroyed to clean (or detect contamination of) the patterning device.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system comprising, for example, suitable directing mirrors and/or a beam expander. In other cases the source may be an integral part of the lithographic apparatus, for example when the source is a mercury lamp. The source SO and the illuminator IL, together with the beam delivery system if required, may be referred to as a radiation system.

The illuminator IL may comprise an adjuster for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may comprise various other components, such as an integrator and a condenser. The illuminator may be used to condition the radiation beam, to have a desired uniformity and intensity distribution in its cross-section.

The radiation beam B is incident on the patterning device (e.g., mask MA), which is held on the support structure (e.g., mask table MT), and is patterned by the patterning device. Having traversed the mask MA, the radiation beam B passes through the projection system PS, which focuses the beam onto a target portion C of the substrate W. With the aid of the second positioner PW and position sensor IF2 (e.g. an interferometric device, linear encoder or capacitive sensor), the substrate table WT can be moved accurately, e.g. so as to position different target portions C in the path of the radiation beam B. Similarly, the first positioner PM and another position sensor IF1 can be used to accurately position the mask MA with respect to the path of the radiation beam B, e.g. after mechanical retrieval from a mask library, or during a scan. In general, movement of the mask table MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the mask table MT may be connected to a short-stroke actuator only, or may be fixed. Mask MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the mask MA, the mask alignment marks may be located between the dies.

The depicted apparatus could be used in at least one of the following modes:

1. In step mode, the mask table MT and the substrate table WT are kept essentially stationary, while an entire pattern imparted to the radiation beam is projected onto a target portion C at one time (i.e. a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the mask table MT and the substrate table WT are scanned synchronously while a pattern imparted to the radiation beam is projected onto a target portion C (i.e. a single dynamic exposure). The velocity and direction of the substrate table WT relative to the mask table MT may be determined by the (de-)magnification and image reversal characteristics of the projection system PS. In scan mode, the maximum size of the exposure field limits the width (in the non-scanning direction) of the target portion in a single dynamic exposure, whereas the length of the scanning motion determines the height (in the scanning direction) of the target portion.

3. In another mode, the mask table MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

At present, particle contamination of patterning devices MA has limited influence of the patterns applied to substrates W. Due to the wavelength of radiation used to pattern the substrates W, small particle contamination of the patterning device MA has little effect on the propagation and patterning of the radiation beam B. Present patterning devices (e.g. reticles) typically use a protective pellicle that is spaced away from the patterning device MA. Any contamination will be deposited on the protective pellicle, and will not form part of the pattern imaged onto the substrate W by the projection system PS. However, with the development of lithographic apparatus, the wavelengths used to pattern substrates W are decreasing. Proposed lithographic apparatus will use EUV radiation (e.g. having a wavelength in the range of 5-20 nm). A protective pellicle can no longer be used, as it will absorb the EUV radiation. It will be appreciated that contamination of the patterning device MA can lead to defects in the patterns applied to the substrate W, and therefore lead to a reduction in the yield of acceptably patterned substrates W.

There are many occasions during the life of a patterning device in which particle contamination can occur. For example, if the cleaning of patterning devices MA is undertaken in a separate facility, independent of the lithographic apparatus, the patterning device may become contaminated after its cleaning during moving it to the lithographic apparatus and loading it onto the support structure MT in the lithographic apparatus. At present, there is no inspection or cleaning of the patterning device MA immediately before loading of the patterning device MA into the lithographic apparatus, or within the apparatus itself. It is only after exposure of the substrate W that defects due to particle contamination are detected in the pattern applied to the substrate W. By this time, the substrate W has already been exposed, and contains a defective pattern. In many circumstances, part of the substrate W is now useless (or may need lengthy repair processes to be reusable), which is costly and reduces the yield.

By providing a cleaning unit CU that is arranged to clean the patterning device MA in-situ, the problem of contaminating the patterning device between initial cleaning at a separate facility and loading it onto the support structure MT is reduced and/or avoided.

Figure 2:
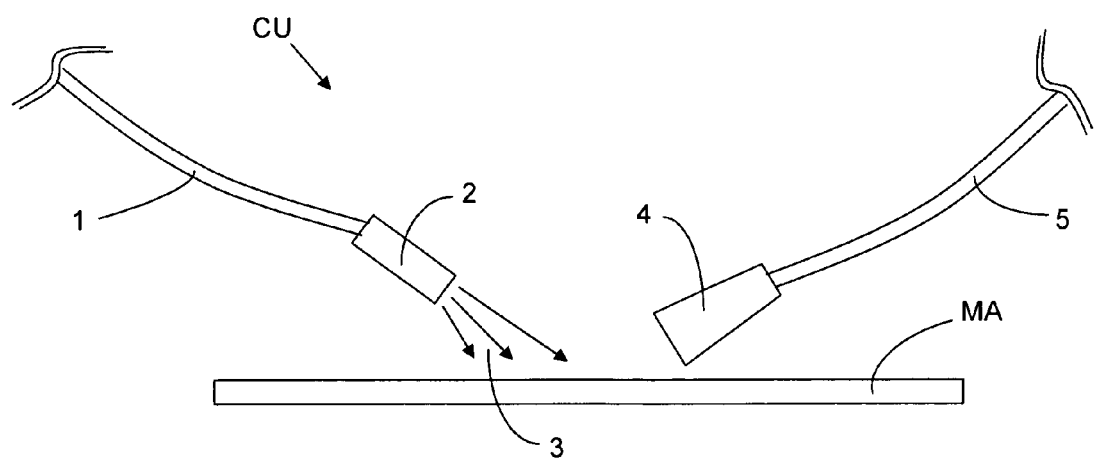
FIG. 2 depicts the cleaning unit of FIG. 1 in more detail.

The cleaning unit CU is shown in more detail, and in use, in FIG. 2. The cleaning unit CU comprises a feed tube 1 and a nozzle 2 in fluid communication with the feed tube 1. The nozzle 2 is directed towards a surface of the patterning device MA to be cleaned. The nozzle 2 may be moved into a desired location relative to the patterning device MA, or the patterning device MA can be moved to a desired location relative to the nozzle 2 (for example, prior to the patterning device MA being loaded onto the support structure MT). In use, carbon dioxide 3 (or any suitable cleaning fluid, and in particular any suitable cleaning gas) is discharged from the end of the nozzle 2 and directed toward the surface of the patterning device MA. The carbon dioxide 3 contacts the surface of the patterning device MA and dislodges particle contaminants (not shown). The carbon dioxide 3 and particle contaminants are then collectively removed by an extraction device e.g. exhaust 4 and exhaust pipe 5. The carbon dioxide 3 and particle contaminants removed by the exhaust may be fed to a reservoir, where the particle contaminants may be filtered out of the carbon dioxide 3 such that the carbon dioxide 3 may be reused. Alternatively, the carbon dioxide 3 and particle contaminants may be simply disposed of. The exhaust 4 and the exhaust pipe 5 may, for example be omitted and the carbon dioxide 3 (or any other suitable cleaning gas) and particle contaminants may then collectively be removed by pumps functioning as the extraction device. The same pumps may also be used in normal use for creating a vacuum within the vacuum chamber of the lithographic apparatus.

By cleaning the patterning device in-situ (i.e. within or in communication with the lithographic apparatus), the level of contamination of the patterning device MA when exposed to radiation is reduced with respect to prior cleaning apparatus and methods. As the patterning device MA is cleaner when used to pattern a substrate W, the resulting pattern should comprise less defects, which will improve the yield. Furthermore, in an extreme ultraviolet lithographic apparatus, the apparatus is provided with a vacuum chamber that is evacuated by pumps. By cleaning the patterning device MA in-situ, the vacuum does not need to be destroyed for the patterning device MA to be cleaned or the patterning device MA need not to be moved outside the vacuum chamber. This may save valuable operating (exposure) time, and reduce the possibility of the patterning device MA becoming contaminated.

The above embodiment has been described by way of example, and it will be appreciated that various modifications may be made thereto. For example, the embodiment described above uses carbon dioxide to clean the patterning device MA, but other suitable fluids, for example any suitable inert gas or a combination of gases could be used. The above embodiment has been described in relation to the use of a nozzle and exhaust, but other fluid delivery and extraction apparatus may be used. These are merely examples of how the present invention may be realized, i.e. cleaning of the patterning device MA in-situ. Any suitable cleaning unit (i.e. a device which cleans the patterning device) may be used. For example, atomic hydrogen (e.g. atomic hydrogen in a gaseous form) may be used instead of inert gas. This is useful for example if the contamination to be removed comprises carbon which has grown onto the patterning device MA. The atomic hydrogen may be provided to the patterning device MA with a nozzle directed to the supporting structure MT so that the patterning device can be cleaned while it is on the supporting structure MT even during exposure saving even further valuable exposure time.

The cleaning unit may also be used to remove contamination from the patterning device MA that is deposited on the patterning device MA while it is in the lithographic apparatus. The cleaning unit may be capable of cleaning a patterned surface of the patterning device MA and may be capable of cleaning a clamping surface of the patterning device MA that is used to clamp the patterning device MA to the support structure MT. For this purpose the cleaning unit CU may be provided with a rotating unit for rotating the patterning device MA such that first the patterned surface can be cleaned, and second the clamping surface of the patterning device MA can be cleaned, or the other way around. The cleaning unit may also be constructed and arranged so that both the patterned surface and clamping surface may be cleaned without rotating the patterning device MA.

The embodiment described above relates to the cleaning of the patterning device MA in-situ. According to another aspect of the present invention, there is provided a detection unit arranged to detect particle contamination of the patterning device MA in-situ. Detection of particle contamination may be undertaken prior to cleaning of the patterning device MA, in conjunction with cleaning of the patterning device MA, after cleaning of the patterning device MA or instead of cleaning the patterning device MA. In providing a detection unit, contamination of a patterning device MA can be detected before applying a pattern to a substrate. Such detection will therefore improve the yield of acceptably patterned substrates W by reducing the number of defective patterns applied thereto.

Figure 3:
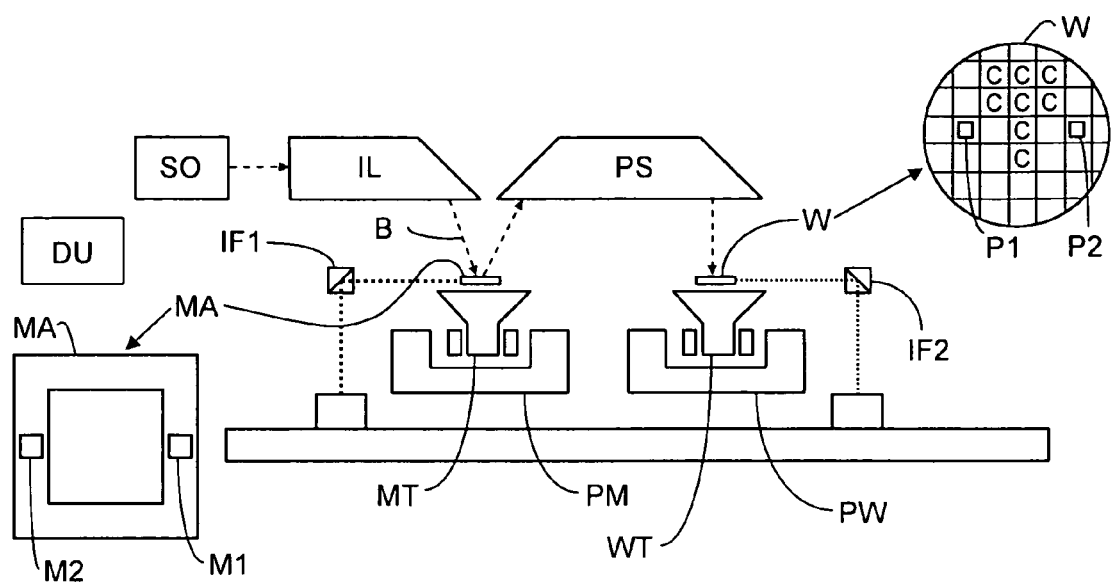
FIG. 3 depicts a lithographic apparatus provided with a detection unit according to another embodiment of the present invention.

FIG. 3 shows a lithographic apparatus identical in form to that shown and described with reference to FIG. 1, with the exception that the cleaning unit CU (shown in FIG. 1) been replaced with a detection unit DU. As with the cleaning unit CU of FIG. 1, the detection DU of FIG. 3 is arranged to detect contamination of the patterning device MA in-situ (i.e. within or in communication with the lithographic apparatus).

Figure 4:
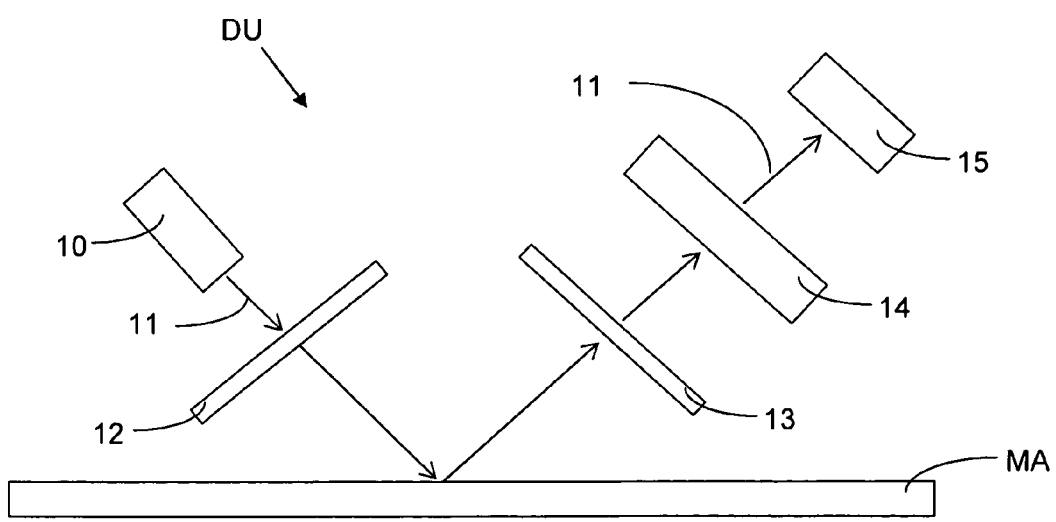
FIG. 4 depicts the detection unit of FIG. 3 in more detail.

An embodiment of the detection unit DU is shown in detail in FIG. 4, which illustrates apparatus (ellipsometric apparatus) performing an ellipsometric analysis of the patterning device MA. The apparatus comprises a radiation source 10, which may be located outside a vacuum chamber and which is arranged to direct a detection beam of radiation 11 towards a part of the surface of the patterning device MA where detection of particle contaminants is required. The detection beam of radiation 11 is polarized by a polarizer 12 before the beam 11 is incident on the patterning device MA. If linearly polarized light of a known orientation is reflected at oblique incidence from a surface then the reflected light is elliptically polarized. The reflected and now elliptically polarized beam 11 passes through a quarter waveplate 13 and an analyzer 14 before being detected by the detector 15. The polarization of the reflected light 11 can be measured using the quarter waveplate and analyzer by varying their respective orientations until no light passes through the analyzer (i.e. until no light is detected by the detector). From the orientations of the quarter waveplate 13 and analyzer 14 when no light is detected, the relative phase change introduced by reflection from the surface of the patterning device MA can be calculated. From the phase change, the size (or thickness) of contamination of the patterning device MA can be calculated in a known manner.

Figure 5:
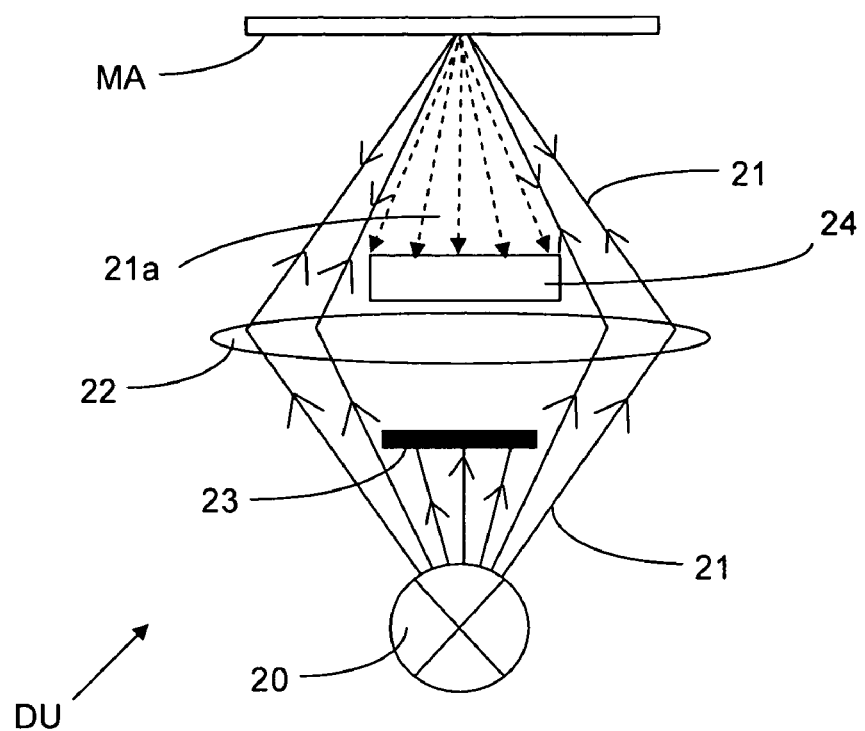
FIG. 5 depicts another embodiment of the detection unit.

It will be appreciated that other detection apparatus and methods may be used to detect contamination of the patterning device MA. For example, another embodiment of the detection unit DU is shown in FIG. 5, which depicts a dark field imaging apparatus. In this embodiment, the detection unit DU comprises a highly divergent light source (or 'point source') 20. Some of the light 21 emitted by the light source 20 is incident on a condenser lens 22 located adjacent the light source 20. Located in-between the condenser lens 22 and the light source 20 is an occulting disc 23. The occulting disc 23 ensures that only highly divergent light is allowed to pass to the condenser lens 22. The condenser lens 22 focuses the highly divergent light (detection beam of radiation) onto the patterning device MA. The light 21 reflects off the patterning device MA. A detector 24 (e.g. a CCD detector) is positioned in-between the patterning device MA and condenser lens 22, such that it faces toward the patterning device MA but does not obstruct light focused onto the patterning device MA. As highly divergent light 21 is incident on the patterning device MA it will, unless scattered, reflect back either side of the detector 24 and will not be detected. However, if the highly divergent light 21 is scattered by contamination (e.g. particulate contamination) on the patterning device MA, a portion of the light 21a will be scattered towards the detector 24. Therefore, bright spots detected by the detector 24 will in fact be caused by light scattered from particulate contaminants on the patterning device MA. Therefore, using relatively simple optical apparatus, (very small) particles can be detected on the patterning device MA.

It will be appreciated that the above embodiments have been described by way of example only, and that various modifications can be made thereto. For example, the above embodiments have been described with reference to ellipsometry and dark field imaging. However, other suitable detection methods and apparatus may be used. The detection unit DU need only be capable of detecting contamination of the patterning device MA. As with the cleaning unit CU, it will be appreciated that the detection unit DU (or apparatus thereof) may be moved to detect contamination of a particular part of the patterning device MA. Conversely, the patterning device MA may be moved toward and relative to the detection unit DU. It may be necessary to scan the surface (or surfaces) of the patterning device MA to detect particle contaminants thereon. In this case, it may be suitable to scan the detection unit DU relative to the patterning device MA, or conversely, scan the patterning device MA relative to the detection unit DU. The detection unit may comprise optics for directing light with a wavelength between 150 and 800 nm to the patterning device.

Although in some instances it may only be necessary to determine whether one surface of the patterning device MA is contaminated, it will often be the case that it is necessary to determine whether either surface of the patterning device is contaminated. For this purpose, the detection unit DU may be provided with a rotating unit for rotating the patterning device MA such that first the patterned surface can be detected, and second the clamping surface of the patterning device MA can be detected, or the other way around. The detection unit may also be constructed and arranged that both the patterned surface and clamping surface may be detected without rotating the patterning device MA.

The detection unit DU may be of any suitable configuration and/or orientation. The field imaging apparatus may be positioned above, below or at an angle with respect to the patterning device MA. When detecting particle contamination on the surface (or surfaces) of the patterning device MA, the patterning device MA may be rotated such that the surface which imparts a pattern to the cross section of the radiation beam B is facing downwards when detection takes place. The patterning device MA is rotated to face downwards to reduce the possibility of additional particle contaminants falling onto the patterning side of the patterning device MA. However, it may be preferable to avoid rotation of the patterning device where possible, for example to save space or time (or even to simplify equipment used to control movement of the patterning device MA). Various techniques may be used where the properties of a first surface can be derived from the (e.g. optical) properties of a second, opposite surface. For example, the dark field imaging technique described above can detect particle contaminants on either surface of the patterning device (where the patterning device is transmissive). In this case, the patterning device may not need to be rotated. Alternatively, data field imaging apparatus may be positioned above and below the patterning device MA, so that two surfaces thereof may be simultaneously scanned for contamination, without needing to rotate the patterning device MA.

The cleaning unit CU and detection unit DU described above have been described as cleaning the patterning device MA and detecting particle contaminants thereon in-situ. In-situ has been described as a location substantially within the lithographic apparatus, or in communication therewith, such that (for example) cleaning of the patterning device or detection of particle contaminants thereon may be undertaken without having to destroy the vacuum which exists in the lithographic apparatus. This is useful for EUV lithography, since a very high vacuum is required with an EUV lithography apparatus. It may also be useful for lithography apparatus which use other wavelengths. Cleaning of the patterning device or detection of particle contaminants thereon may be undertaken without having to transport the patterning device to a separate cleaning/detection facility, remote from the lithographic apparatus, reducing the possibility of contaminating the patterning device during transport.

Figure 6A:
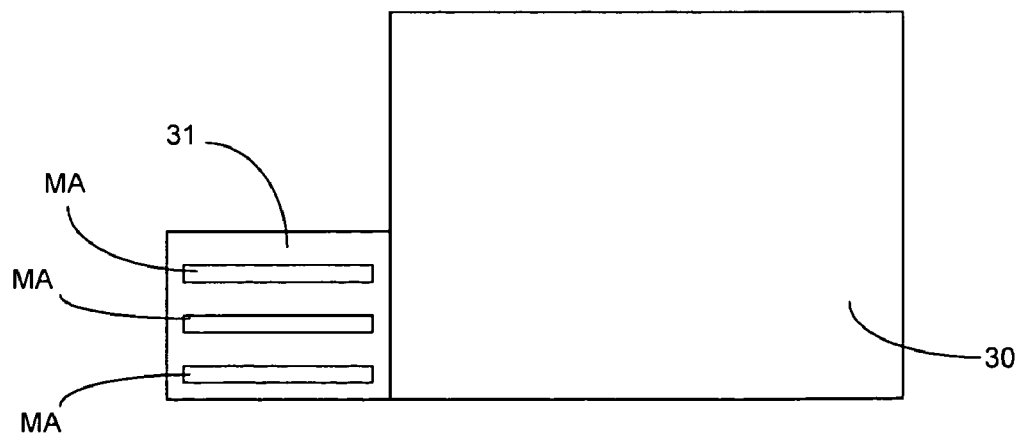
FIGS. 6A-6C depict simplified views of the layout of the lithographic apparatus according to embodiments of the present invention.

FIG. 6A illustrates a schematic view of a lithographic apparatus in accordance with an embodiment of the present invention. The lithographic apparatus has been shown in an extremely simplified format to aid the explanation of the term 'in-situ' used herein. The lithographic apparatus comprises a first chamber 30 (e.g. an evacuated or vacuum chamber 30), where exposure of the substrates W takes place, and a second or transfer chamber 31 in communication with the evacuated chamber 30. The second chamber 31 is used to introduce objects to the evacuated chamber 30, and to remove objects from the evacuated chamber 30. For example, different or replacement patterning devices MA may be located in the second chamber 31 for introduction into the evacuated chamber 30. A robot chamber (not shown) may for example form part of the first chamber 30, and may be arranged to handle objects received from the second chamber 31. The robot chamber may be provided with a gripping device to grip and handle the objects.

Figure 6B:
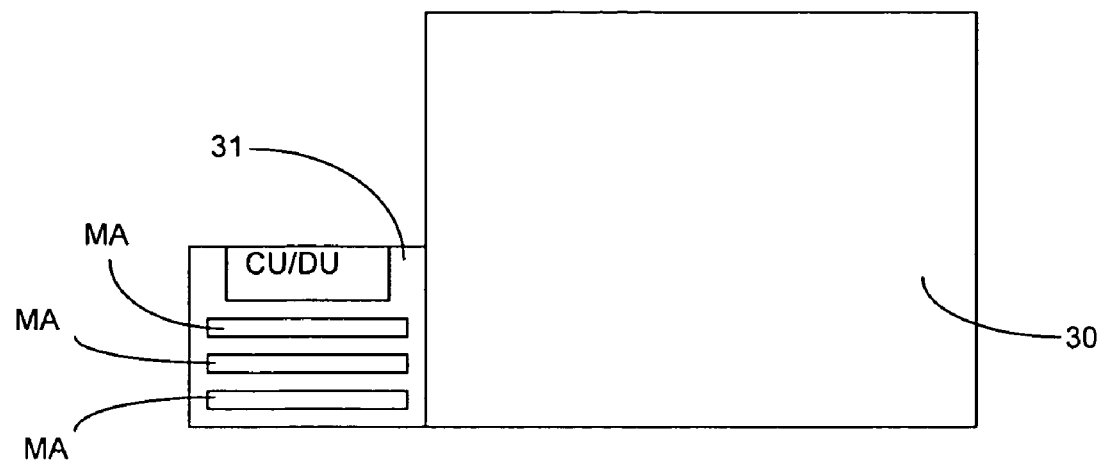

FIG. 6B shows a cleaning unit CU and/or detection unit DU located in the second chamber 31 (e.g. patterning device MA storage chamber 31). By locating the cleaning unit CU and/or detection unit DU in the patterning device MA storage chamber 31, the substrates W may be cleaned and/or scanned for contamination in-situ. The lithographic apparatus is self-contained, such that when detection or cleaning has taken place in the patterning device MA storage chamber 31, no more (or at least, very little) contamination can be added to the surface of the patterning device MA when it is introduced from the patterning device MA storage chamber 31 into the evacuated chamber 30. Indeed, the patterning device MA storage chamber 31 is often evacuated, sometimes to the same extent as the evacuated chamber 30 to reduce contamination. In an embodiment, a door may be provided between the patterning device MA storage chamber 31 and the evacuated chamber. The door may be closed, following which cleaning of a patterning device MA may take place. Any gas which passes into the patterning device storage chamber 31 may be pumped out, to restore the vacuum, before the door is opened. Therefore, the patterning device MA can be cleaned without destroying the vacuum in the evacuated chamber. Since the patterning device storage chamber 31 forms part of the lithographic apparatus, cleaning of the patterning device MA takes place in-situ in the lithographic apparatus.

Figure 6C:
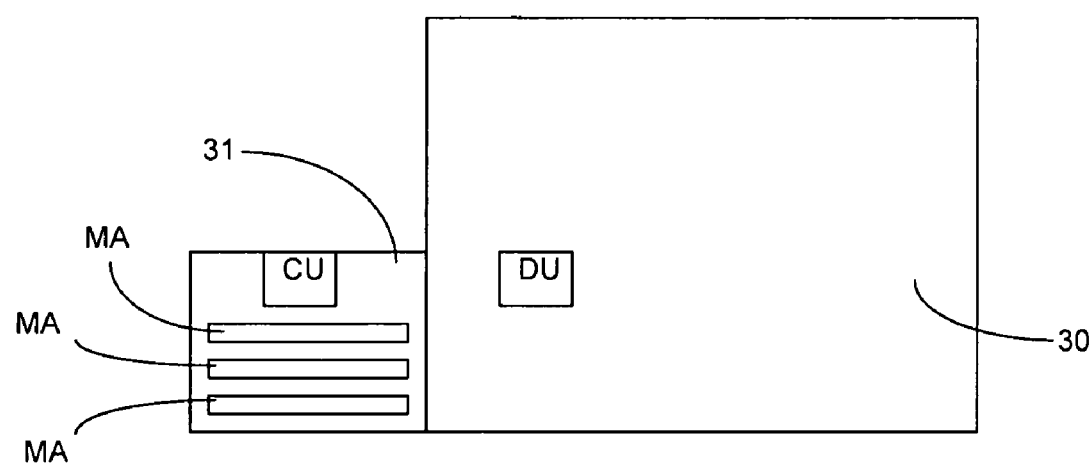

FIG. 6C illustrates a modification of the lithographic apparatus of FIG. 6B. Specifically, the cleaning unit CU is now located in the patterning device MA storage chamber 31, whereas the detection unit DU is located in the evacuated chamber 30. It will be appreciated that the cleaning unit CU and detection unit DU may be located in any suitable location within the lithographic apparatus. In some circumstances however, it may be desirable to locate the cleaning unit away from the evacuated chamber 30, so that any particle contaminants removed from the surface of the patterning device MA by, for example, exposure to high pressure carbon dioxide are not deposited on other sensitive surfaces of the lithographic apparatus within the evacuated chamber 30.

Whereas the cleaning unit and detection unit have been described as being located within an evacuated vacuum chamber 30 or a second vacuum chamber 31 in communication therewith, the cleaning unit CU and detection unit DU may be placed in any suitable location. An advantage of having the cleaning unit and detection unit within the vacuum chambers may be that patterning devices MA only may be transported outside vacuum within a contamination protection box. Cleaning and detection of contamination may not be possible when the patterning device MA is within the box. A cleaning unit CU and/or detection unit DU outside the vacuum system may need therefore a system for opening the box and removing the patterning device MA which imposes risks of contamination. The cleaning unit CU and/or detection DU may be located anywhere where cleaning and detection may be undertaken in-situ (i.e. within or in communication with the lithographic apparatus) so that, for example, a vacuum need not be destroyed for cleaning and/or detection to take place. For example the cleaning unit CU and/or detection unit DU may be located at one of a number of handling or stages of the patterning device MA (e.g. adjacent (which includes in or on) a handling or storage stage).

It will be appreciated that the lithographic apparatus may comprise a detection unit DU and/or a cleaning unit CU. The detection unit DU and cleaning unit CU may be located in close proximity to each other, or at different parts of the lithographic apparatus, far from one another. The detection unit DU and cleaning unit CU may cooperate, such that the surface is scanned for contamination by the detection unit DU, before it is cleaned (if necessary) by the cleaning unit CU. This process may be repeated until the patterning device MA is deemed clean enough to be used to pattern a substrate.

Although the present invention is applicable to all types of lithographic apparatus, it is particularly relevant to lithographic apparatus that use EUV radiation to apply a pattern to a substrate W. This is due to the fact that particle contamination is a particular problem lithographic apparatus that employ such radiation to pattern a substrate, as described above.

Although the specific detection units and cleaning units described above in relation to FIGS. 2, 4 and 5 have been referred to as being in-situ in the lithographic apparatus, it will be appreciated that they may be provided at some other location.

It will be appreciated that in general in the above described embodiments, the patterning device MA is moved to a cleaning unit or detection unit which is located away from the normal location of the pattern device in use. This may be expressed as saying that the patterning device is moved to a cleaning location or detection location. The cleaning location or detection location may comprise the patterning device storage chamber 31, or may comprise some other particular location within the lithographic apparatus. The patterning device MA may be moveable using a patterning device handler, examples of which are well known in the art. In some instances the cleaning unit or the detection unit may be moveable.

The cleaning and detection unit may also be constructed and arranged to clean or detect contamination on a clamping surface of the support structure MT or of the clamping surface of the substrate table WT. Contamination on the clamping surface of the support structure or the substrate table MT may also lead to deteriorated exposures from the mask MA on the substrate W.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin-film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

Where references have been made in the above description to the use of carbon dioxide, it will be understood that this is an example only, and that other suitable gases may be used. For example, an inert gas or a combination of inert gases may be used.

The terms "radiation" and "beam" as used herein encompass all types of electromagnetic radiation, including ultraviolet (UV) radiation (e.g. having a wavelength of or about 365, 355, 248, 193, 157 or 126 nm) and extreme ultra-violet (EUV) radiation (e.g. having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

While specific embodiments of the invention have been described above, it will be appreciated that the invention may be practiced otherwise than as described. For example, the invention may take the form of a computer program containing one or more sequences of machine-readable instructions describing a method as disclosed above, or a data storage medium (e.g. semiconductor memory, magnetic or optical disk) having such a computer program stored therein.

The descriptions above are intended to be illustrative, not limiting. Thus, it will be apparent to one skilled in the art that modifications may be made to the invention as described without departing from the scope of the claims set out below.

What is claimed is:

1. A lithographic apparatus comprising:
   an illumination system configured to condition an extreme ultraviolet radiation beam;
   a support configured to support a patterning device, the patterning device being configured to impart the extreme ultraviolet radiation beam with a pattern in its cross-section to form a patterned extreme ultraviolet radiation beam;
   a substrate table constructed to hold a substrate;
   a projection system provided with reflective optics configured to project the patterned extreme ultraviolet radiation beam onto a target portion of the substrate;
   a vacuum chamber assembly constructed to create a vacuum environment, the vacuum chamber assembly including a first vacuum chamber in which the support is located, and a second vacuum chamber in communication with the first chamber, the first and second vacuum chambers being configured to allow the introduction and removal of the patterning device to and from the first vacuum chamber via the second vacuum chamber; and
   a detection unit arranged within the second vacuum chamber to detect contamination on the patterning device,
   wherein the first and second vacuum chambers are configured to allow contamination detection on the patterning device in the second vacuum chamber when exposure using another patterning device occurs in the first vacuum chamber.

2. A lithographic apparatus according to claim 1, wherein the detection unit is provided in a detection location to which the patterning device is movable for contamination detection.

3. A lithographic apparatus according to claim 1, wherein the detection unit comprises optics for directing a detection beam of radiation to the patterning device.

4. A lithographic apparatus according to claim 1, wherein the detection unit comprises optics for directing light to the patterning device.

5. A lithographic apparatus according to claim 4, wherein the detection unit comprises optics for directing light with a wavelength between 150 and 800 nm to the patterning device.

6. A lithographic apparatus as claimed in claim 1, wherein the detection unit comprises a dark field imaging apparatus.

7. A lithographic apparatus as claimed in claim 1, wherein the detection unit comprises an ellipsometric apparatus arranged to undertake an ellipsometric analysis of a surface of the patterning device.

8. A lithographic apparatus as claimed in claim 1, further comprising a patterning device handling device for transporting the patterning device, and wherein the detection unit is located adjacent the patterning device handling device.

9. A lithographic apparatus according to claim 1, wherein the apparatus further comprises a cleaning unit for cleaning the patterning device.

10. A method of detecting contamination on a patterning device of a lithographic apparatus, the method comprising:
    moving the patterning device to a detection unit in a first vacuum chamber;
    detecting contamination within the first vacuum chamber with the detection unit;
    cleaning at least a portion of the patterning device in the first vacuum chamber; and
    moving the cleaned patterning device to a second vacuum chamber to pattern a beam of radiation, the second vacuum chamber in communication with the first vacuum chamber, and the first and second vacuum chambers configured to allow the detecting and cleaning of another patterning device in the first vacuum chamber when the patterning occurs in the second vacuum chamber.

11. A method according to claim 10, wherein the detecting comprises directing a detection beam of radiation to the patterning device.

12. A lithographic apparatus comprising:
    an illumination system configured to condition an extreme ultraviolet radiation beam;

a support configured to support a patterning device, the patterning device being configured to impart the extreme ultraviolet radiation beam with a pattern in its cross-section to form a patterned extreme ultraviolet radiation beam;

a substrate table constructed to hold a substrate;

a projection system provided with reflective optics configured to project the patterned extreme ultraviolet radiation beam onto a target portion of the substrate;

a vacuum chamber assembly constructed to create a vacuum environment, the vacuum chamber assembly including a first vacuum chamber in which the support is located, and a second vacuum chamber in communication with the first chamber, the first and second vacuum chambers being configured to allow the introduction and removal of the patterning device to and from the first vacuum chamber via the second vacuum chamber; and a detection unit arranged within the first vacuum chamber to detect contamination on the patterning device.

wherein the first and second vacuum chambers are configured to allow detection or exposure of the patterning device in the first vacuum chamber when cleaning of another patterning device occurs in the second vacuum chamber.

13. A lithographic apparatus according to claim 12, wherein the detection unit is provided in a detection location to which the patterning device is movable for contamination detection.

14. A lithographic apparatus according to claim 12, wherein the detection unit comprises optics for directing a detection beam of radiation to the patterning device.

15. A lithographic apparatus according to claim 12, wherein the detection unit comprises optics for directing light to the patterning device.

16. A lithographic apparatus according to claim 15, wherein the detection unit comprises optics for directing light with a wavelength between 150 and 800 nm to the patterning device.

17. A lithographic apparatus as claimed in claim 12, wherein the detection unit comprises a dark field imaging apparatus.

18. A lithographic apparatus as claimed in claim 12, wherein the detection unit comprises an ellipsometric apparatus arranged to undertake an ellipsometric analysis of a surface of the patterning device.

19. A lithographic apparatus as claimed in claim 12, further comprising a patterning device handling device for transporting the patterning device, and wherein the detection unit is located adjacent the patterning device handling device.

20. A lithographic apparatus according to claim 12, wherein the apparatus further comprises a cleaning unit for cleaning the patterning device.

* * * * *